United States Patent [19]

Luiset et al.

[11] Patent Number: 4,673,351
[45] Date of Patent: Jun. 16, 1987

[54] CONTRA-ANGLE FOR DENTAL HANDPIECE

[75] Inventors: Jean-Jacques Luiset, Geneva, Switzerland; Michel Seigneurin, Douvaine, France

[73] Assignee: Micro-Mega S.A., Besancon, France

[21] Appl. No.: 795,998

[22] Filed: Nov. 7, 1985

[30] Foreign Application Priority Data

Nov. 7, 1984 [FR] France .................. 84 17334
Feb. 15, 1985 [FR] France .................. 85 02692

[51] Int. Cl.⁴ .......................... A61C 1/08; A61C 3/00
[52] U.S. Cl. ................................................ 433/29
[58] Field of Search ......................................... 433/29

[56] References Cited

U.S. PATENT DOCUMENTS

| 2,932,294 | 4/1960 | Fourestier et al. | 433/29 |
| 3,109,238 | 11/1963 | Marks | 433/29 |
| 4,398,885 | 8/1983 | Loge et al. | 433/29 |

FOREIGN PATENT DOCUMENTS

| 1123034 | 9/1956 | France | 433/29 |
| 1412622 | 11/1975 | United Kingdom | 433/29 |

Primary Examiner—John J. Wilson
Attorney, Agent, or Firm—Bruce L. Adams; Robert E. Burns; Emmanuel J. Lobato

[57] ABSTRACT

The contra-angle is provided with means for illuminating the site of treatment. The light source is incorporated inside the body of the contra-angle, and in front of this light source is inserted an optical element arranged to deflect the light rays towards the site of treatment. This optical element comprises a total reflection prism embedded in a recess in the body of the contra-angle.

8 Claims, 2 Drawing Figures

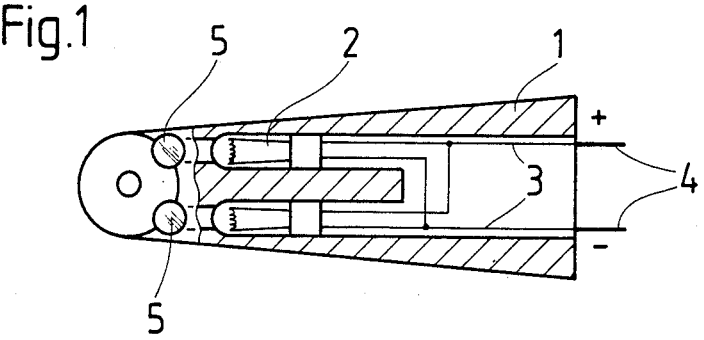
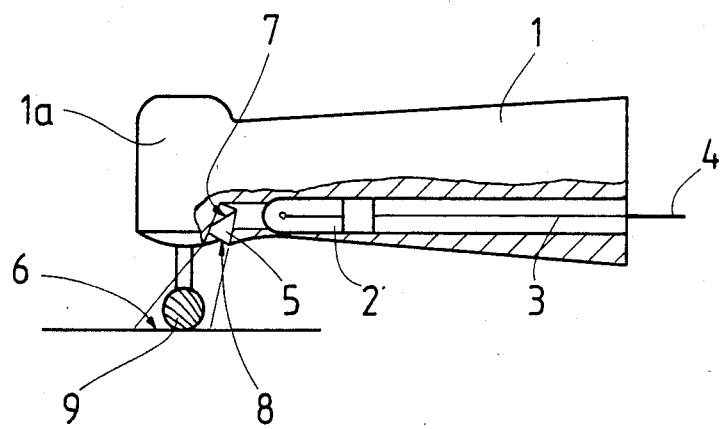

CONTRA-ANGLE FOR DENTAL HANDPIECE

BACKGROUND OF THE INVENTION

The invention concerns a contra-angle for a dental handpiece provided with means for illuminating the site of treatment.

In order to facilitate the work of dental surgeons, there has already cropped up the idea of incorporating in the working instrument, that is, in the dental handpiece itself, lighting means which are arranged to illuminate the site of treatment.

European Pat. No. 34237, for example, proposes lighting means with optical fibers which pass through the different parts of the handpiece and whose light emitting ends are directed towards the end of the tool.

Other systems have also been envisaged, including particularly small electric bulbs incorporated in the end of the head of the contra-angle and directed towards the site of treatment.

The prior art envisaged up to now does not give full satisfaction and exhibits several disadvantages. In the case of bulbs incorporated in the end of the head of the contra-angle, their major disadvantage is their bulkiness. These bulbs must be placed in a very restricted zone into which cooling fluid supply pipes also open out and, even when using minibulbs, it is difficult to reduce their bulkiness optimally. Moreover, since these bulbs have to be placed as close as possible to the site of working, they may come into contact with the enamel of the teeth and may be subjected to impacts which cause damge to the bulbs. It is furthermore impossible to perfectly seal off the space between these bulbs and their housing from the cooling liquid or dust, while leaving therein a sufficient play to be perfectly accessible for the purpose of replacing the bulbs if necessary. In the case of optical fibers, if they are embedded up to the end of the head, it is difficult to orient their light-emitting ends appropriately towards the site of treatment, because they cannot be bent at a sufficient angle and, if they protrude from the handpiece before the end, they are no longer protected and their front end from which the light emerges may be damaged during treatment, which risks decreasing the light flux considerably.

SUMMARY OF THE INVENTION

The present invention proposes to provide a contra-angle for a dental handpiece provided with water-tight lighting means whose light rays are directed in a precise manner towards the site of treatment.

For this purpose, the contra-angle for a handpiece according to the invention is characterised in that the light source is incorporated inside the body of the contra-angle, and in front of this light source is inserted an optical element which deflects the light rays, embedded in a recess situated close to the head of the contra-angle and arranged so as to deflect the light rays towards the site of treatment.

The advantages of this device are obvious. The light source consisting of a bulb or unbent optical fibers, incorporated completely inside the body of the contra-angle, is therefore protected by the contra-angle itself. The optical element, which is preferably inserted as far as possible in the body of the contra-angle so as practically not to project from the peripheral wall of the body, does not risk being damaged by impacts or by contact with the teeth. Furthermore, this optical element, being embedded in the wall of the contra-angle, ensures water-tightness of the housing of the light source to avoid the entry of dust or water splashing during treatment.

The invention will be described in the following description of an embodiment of the contra-angle in conjunction with the attached drawing.

BRIEF DESCRIPTION OF THE DRAWINGS

FIG. 1 is a schematic and partly sectional view from the bottom of the head of the contra-angle; and FIG. 2 is a schematic side-face view thereof.

DESCRIPTION OF THE PREFERRED EMBODIMENT

In the front portion of the body 1 of the contra-angle, close to the head 1a in which the dental instrument or tool 9 is vertically accomodated, are mounted two bulbs 2 connected by wires 3 to plugs 4 which allow them to be connected to wires coming from the handpiece, not shown. In front of each bulb 2 is inserted a total reflection prism 5 embedded provided on a recess in the body of the contra-angle, and arranged so as to totally deflect the light rays towards the site of treatment 6, i.e., towards the working range of the tool 9.

This prism 5, being embedded in the body 1, forms a water-tight stopper and prevents any infiltration of dust or water into the housing of the bulb 2 and into the contra-angle. This prism 5 is positioned in the most appropriate way for enabling its working face 7 to undergo total reflection of the light rays, which emerge via its front face 8. Its angle of inclination is selected so that the light rays are directed exclusively towards the site of treatment 6 of the instrument 9. Total reflection gives optimum light output, without loss.

In the embodiment shown in the drawings, it can be seen that the prism is almost completely inserted in the body of the contra-angle; however, it would be equally possible to embed it completely so that it does not project from the peripheral wall of the body.

Other embodiments of this device may be provided, particularly in respect of the light source which may be embodied by means of optical fibers inserted completely in the body of the contra-angle with a rectilinear path, the prism or other optical element allowing the light rays to be directed towards the site of working.

It would also be possible to provide a different optical element instead of the prism, for example, a mirror oriented so as to reflect the light rays onto the desired site.

What is claimed is:

1. A contra-angle for a dental handpiece provided with means for illuminating the site of treatment, comprising a head, a body extending from the head, the body having means defining a recess disposed thereon adjacent to the head, at least one light source incorporated inside the body for emitting light rays, and a total reflection prism disposed in front of the light source for receiving the light rays, said total reflection prism being embedded in the recess and arranged so as to totally deflect the light rays towards the site of treatment.

2. A contra-angle according to claim 1, wherein said total reflection prism practically does not project from the outer surface of the body of the contra-angle.

3. A contra-angle for a dental handpiece comprising: a dental tool; a head for vertically supporting the dental tool; a body horizontally extending from the head, the body having means defining a housing longitudinally extending inside the body and means defining a recess thereon disposed adjacent the head and optically communicating with the housing; light source means disposed in the housing for emitting light rays toward the head; and a total reflection prism disposed in the recess for receiving the light rays and for totally reflecting the light rays to illuminate a working range of the dental tool.

4. A contra-angle according to claim 3; wherein the total reflection prism is embedded in the recess without protruding outwardly therefrom.

5. A contra-angle according to claim 4; wherein the embedded total reflection prism includes a water-tight stopper for the housing.

6. A contra-angle according to claim 3; wherein the light source means comprises a pair of light bulbs.

7. A contra-angle according to claim 6; including a pair of the recesses corresponding to the pair of the light bulbs.

8. A contra-angle according to claim 7; including a pair of total reflection prisms disposed in respective ones of the pair of recesses.

* * * * *